(12) United States Patent
Lin

(10) Patent No.: US 7,001,339 B2
(45) Date of Patent: *Feb. 21, 2006

(54) ASSESSMENT OF CONCENTRATION OF INHALATIONAL COMPOUNDS IN THE BRAIN

(76) Inventor: Chung-Yuan Lin, 5501 Kenwood Ave., Chicago, IL (US) 60637

( * ) Notice: Subject to any disclaimer, the term of this patent is extended or adjusted under 35 U.S.C. 154(b) by 462 days.

This patent is subject to a terminal disclaimer.

(21) Appl. No.: 10/425,360

(22) Filed: Apr. 29, 2003

(65) Prior Publication Data

US 2003/0202940 A1    Oct. 30, 2003

Related U.S. Application Data

(62) Division of application No. 09/811,316, filed on Mar. 16, 2001, now Pat. No. 6,579,511.

(51) Int. Cl.
  *A61B 5/08*  (2006.01)
  *A61K 49/00*  (2006.01)
(52) U.S. Cl. .......... 600/532; 600/529; 424/9.1
(58) Field of Classification Search ........ 600/529–544, 600/309; 424/9.1
  See application file for complete search history.

(56) References Cited

U.S. PATENT DOCUMENTS 4,718,432 A * 1/1988 Kimura et al. .............. 600/431
5,775,330 A * 7/1998 Kangas et al. .............. 600/544
5,891,050 A * 4/1999 Gansler et al. .............. 600/544
6,540,691 B1 * 4/2003 Phillips ...................... 600/532
6,579,511 B1 * 6/2003 Lin ............................ 424/9.1
6,585,645 B1 * 7/2003 Hutchinson ................. 600/300

OTHER PUBLICATIONS

C. Y. Lin. *Uptake of Anaesthetic Gases and Vapours.* Anaesth Intens Care 1994: 22: 363-373.

* cited by examiner

*Primary Examiner*—Robert L. Nasser
*Assistant Examiner*—Navin Natnithithadha
(74) *Attorney, Agent, or Firm*—Fish & Richardson P.C.

(57) ABSTRACT

This invention directs to a method of assessing the concentration of an inhalational compound in the brain of a subject. The method includes administering a gas containing the compound into a subject to fill the pulmonary functional residual capacity, which is defined as the remaining lung volume at the end of an unforced respiration. The method also includes measuring an inspired compound concentration ($C_i$) and an expired compound concentration ($C_e$) after having filled the functional residual capacity with the gas. Therefore, a mixed venous compound concentration ($C_{b'}$) can be assessed based on the formula $C_{b'}=[C_i(M-1)+C_e]/M$, in which M is an alveolar membrane factor for the compound; and a brain compound concentration ($C_b$) can be assessed based on the formula $C_b=(C_e+C_{b'})/2$.

7 Claims, No Drawings

ASSESSMENT OF CONCENTRATION OF INHALATIONAL COMPOUNDS IN THE BRAIN

RELATED APPLICATION

This application is a divisional application and claims priority to U.S. application Ser. No. 09/811,316, filed Mar. 16, 2001 now U.S. Pat. No. 6,579,511, the content of which is incorporated herein by reference.

TECHNICAL FIELD

This invention relates to a method of assessing the concentration of an inhalational compound (e.g., an anesthetic) in the brain of a subject after administration of the compound.

BACKGROUND

Minimum Alveolar Concentration (MAC) was introduced in 1964 as a standard of assessing the depth of anesthesia. It is defined as an anesthetic concentration in the alveolar that prevents a response to a painful stimulus in 50% of subjects. Such a definition does not incorporate the time required for an anesthetic concentration in the brain to reach equilibrium with the anesthetic concentration in the alveolar. See Lin, C. Y. (1994) *Anesth Intens Care* 22: 362–373. Thus, the MAC standard cannot be used to accurately assess the depth of anesthesia.

Practically, most anesthesiologists determine the depth of anesthesia based oil exterior symptoms in the patient, such as ocular myosis or abnormal blood pressure. However, these symptoms vary from patient to patient, and reliance on them inevitably involves subjective judgment of the anesthesiologists. Thus, other methods have been developed. For example, one method includes repeatedly administering stimuli to a patient, recording the patient's electrical brain activity after each stimulus, and transforming the record as an indication of the depth of anesthesia. See International Patent Publication No. WO 91/19453.

There remains a need for an objective method for assessing the depth of anesthesia.

SUMMARY

In one aspect, this invention directs to a method of assessing the concentration of an inhalational compound in the brain of a subject. Examples of such a compounds include, not limit to, anesthetics (e.g., isoflurane, haloflurane, desflurane, sevoflurane, enflurane, ether, or nitrous oxide) or non-anesthetics (e.g., carbon dioxide or nitrogen). This method includes (1) administering a gas containing an inhalational compound into a subject to fill the pulmonary functional residual capacity; (2) after having filled the functional residual capacity with the gas, measuring an inspired compound concentration ($C_{i'}$) and an expired compound concentration ($C_{e'}$); (3) assessing a mixed venous compound concentration ($C_b$) based on Formula I: $C_b=[C_{i'}(M-1)+C_{e'}]/M$, in which M is an alveolar membrane factor for the compound; and (4) assessing a compound concentration in the brain ($C_b$) based on Formula II: $C_b=(C_{e'}+C_{b'})/2$. The alveolar membrane factor M, as will be described below, is mostly a constant parameter for each inhalational compound, may slightly vary among different subjects. It can be assessed based on Formula III: $M=1-(C_e/C_i)$, in which $C_i$ and $C_e$ are an inspired compound concentration and an expired compound concentration, respectively, measured at the time when about 90% (i.e., 85–95%) of the functional residual capacity is filled with the gas.

In another aspect, the invention features an article that includes a machine-readable medium that stores machine-executable instructions. Such instructions causes a machine to receive values representing the concentration of a compound administered in a gas into a subject to fill the pulmonary functional residual capacity. The values include an inspired compound concentration ($C_{i'}$) and an expired compound concentration ($C_{e'}$), wherein the inspired compound concentration ($C_{i'}$) and the expired compound concentration ($C_{e'}$) are measured after having filled the functional residual capacity with the gas. The instructions also cause the machine to output a representation of a compound concentration in the brain ($C_b$), in which the representation of the compound concentration in the brain ($C_b$) can be assessed by the formula $C_b=(C_{e'}+C_{b'})/2$, wherein $C_{b'}=[C_{i'}(M-1)+C_{e'}]/M$, M is a given alveolar membrane factor for the compound. Alternatively, the values further include a second inspired compound concentration ($C_i$) and a second expired compound concentration ($C_e$), in which $C_i$ and $C_e$ are measured at the time when about 90% of the functional residual capacity is filled with the gas. M is assessed based by the formula $M=1-(C_e/C_i)$. The instructions may further cause the machine to trigger a detector to sample the compound concentration at the time when about 90% of the functional residual capacity is filled with the gas; monitor a time interval; and trigger the detector to sample the compound from an inspiration and an expiration after filling the functional residual capacity of the subject.

In still another aspect, the invention features an apparatus that includes a display and a processor. The processor can be configured to receive values representing the concentration of a compound administered in a gas into a subject to fill the pulmonary functional residual capacity. The values include an inspired compound concentration ($C_{i'}$) and an expired compound concentration ($C_{e'}$), wherein the inspired compound concentration ($C_{i'}$) and the expired compound concentration ($C_{e'}$) are obtained after having filled the functional residual capacity with the gas. The processor can be also figured to control the display to depict a representation of a compound concentration in the brain ($C_b$), in which the representation of the compound concentration in the brain ($C_b$) is assessed by the formula $C_b=(C_{e'}+C_{b'})/2$, wherein $C_{b'}=[C_i(M-1)+C_{e'}]/M$, and M is an alveolar membrane factor for the compound.

Other advantages or feature of this invention will be apparent from the following detailed description thereof.

DETAILED DESCRIPTION

This invention is based on the discovery of a correlation between an inhalational compound concentration in the brain and the average of an expired compound concentration and a mixed venous concentration.

More specifically, a study was conducted on 16 patients with physical status of American Society of Anesthesiologists Class I and II. See American Society of Anesthesiologists: New classification of physical status. (1963) *Anesthesiology* 24: 111. Each patient was anesthesized with isoflurane, which was administered together with oxygen, air, and nitrous oxide. Catheters were placed in each patient's radial artery and internal jugular bulb for blood sampling. Simultaneously, the inspired isoflurane concentration and the expired isoflurane concentration were recorded. For a total of 192 measurements, a good correlation (R=0.907, R²=0.823) was found between the average of an isoflurane concentration in the redial artery (A) and an isoflurane concentration in the internal jugular bulb (J) and the average of an expired isoflurane concentration ($C_{e'}$) and an estimated mixed venous isoflurane concentration ($C_{b'}$). The term "mixed venous isoflurane concentration" refers to an isoflurane concentration in venous blood from inferior and superior vena, cave, and coronary sinus. The correlation can be expressed as:

$$(A+J)/2=(C_{e'}+C_{b'})/2.$$

Since A represents an isoflurane concentration in the blood that flows into the brain, and J represents an isoflurane concentration in the blood that flows out from the brain, the average of A and J, (A+J)/2, represents the isoflurane compound concentration in the brain ($C_b$). In other words, $C_b$=(A+J)/2. Accordingly:

$$C_b=(C_{e'}+C_{b'})/2.$$

As will be discussed below, $C_{b'}$, like $C_{e'}$, can also be assessed based on an inspired isoflurane concentration and an expired isoflurane concentration. Therefore, without blood sampling, the concentration of an inhalational compound in the brain call be assessed based on measurements of inspired and expired compound concentrations, thereby providing an objective method for determining the depth of anesthesia.

To practice the method of this invention, an inhalational compound-containing gas is delivered to a subject to replace the air in a space called the functional residual capacity (FRC). The FRC is the remaining lung volume at the end of a quiet respiration. Typically, its volume is about 2,500 cc. See Nunn, J. F. (1977) *Applied respiratory physiology* 2$^{nd}$ Ed. London Boston Butterworth & Co. pp 4–5. Initially, the FRC is filled with air, which is gradually replaced by the gas. The exchange normally requires a few minutes. After 3–4 min, 85–95% of the FRC is filled with the gas. As the gas penetrates the alveolar membrane (which separates the gas in the alveoli from venous blood flowing through the pulmonary capillaries), it is picked up by the pulmonary capillary blood flow, delivered to various organs including the brain, and continuously circuited.

As the gas penetrats the alveolar membrane and enters the pulmonary capillary blood flow, it must follow the Fick's principal. See Katzung, R. G. (1998) *Basic principles, introduction in basic and clinical pharmacology Appleton-Lange* p 5. The Fick's principal defines the rate of penetrating the alveolar membrane as:

$$DAk/x \ (C_i-C_{b'})$$

D is a diffusion constant, A is the area of the membrane (proportional to the pulmonary capillary flow or cardiac output), k is a solubility coefficient, x is the thickness of the membrane, $C_i$ is an inspired compound concentration, and $C_{b'}$ is the mixed venous compound concentration. Assuming that the pulmonary capillary flow or the cardiac output is constant, then, for a given inhalational compound, DAk/x is a constant. This constant DAk/x is defined as a membrane factor, M, which varies from one inhalational compound to another. For example, halothane, isoflurane, methoxyflurane, and desflurane have M values of 0.5, 0.4, 0.8, and 0.2, respectively. Since the membrane factor may vary slightly among patients, a more precise determination of the membrane factor can be performed as described below.

The rate of penetrating the alveolar membrane DAk/x ($C_i-C_{b'}$) can be expressed as:

$$M(C_i-C_{b'}), \text{ in which } M \text{ is } DAk/x.$$

When measuring an uptake of an inhalational compound-containing gas in each breathing cycle, the rate of the uptake is a function of a difference between the inspired concentration ($C_i$) and the expired concentration ($C_e$). The difference can be expressed as:

$$C_i-C_e.$$

$C_i-C_e$ and $M(C_i-C_{b'})$ both represent the rate of uptake of an inhalational compound:

$$C_i-C_e=M(C_i-C_{b'}), \text{ or}$$

$$M=(C_i-C_e)/(C_i-C_{b'}).$$

During the initial introduction of an inhalational compound (before the FRC is filled with the gas), the membrane factor M for an individual can be approximated by assuming $C_b'$=0:

$$M=(C_i-C_e)/C_i=1-(C_e/C_i).$$

At the stage of anesthesia (after the FRC is filled with the gas), the equation: $C_{i'}-C_{e'}=M(C_{i'}-C_{b'})$ can be used to calculate the compound concentration in the mixed venous blood ($C_{b'}$), in which $C_{i'}$ and $C_{b'}$ are the inspired compound concentration and the expired compound concentration, respectively:

$$C_{b'}=[C_{i'}(M-1)+C_{e'}]/M.$$

As discussed above, $C_b$=(A+J)/2 and (A+J)/2=($C_{e'}+C_{b'}$)/2, the compound concentration in the brain ($C_b$) can be expressed as:

$$C_b=(C_{e'}+C_{b'})/2.$$

Thus, with measurements of the expired compound concentration ($C_{e'}$) and the mixed venous compound concentration ($C_{b'}$), the compound concentration in the brain ($C_b$) can be readily obtained. Below are two examples of how to assess brain anesthetic concentrations by this method.

An endo-tracheal intubation is performed for administering a gas containing a desflurane to a patient. A tube is connected to the circle system of an anesthesia machine consisting of gas flowmeters, a compound vaporizer, supply of oxygen, air and nitrous oxide gas, and a ventilator (e.g., Detex-Ohmeda, Finland, or Drager, Germany). The gas is then delivered to the patient by the anesthesia machine. Desflurane is vaporizered, taking up 6–8% of the total gas, and delivered at a flow rate of 3,000 mL/min. Near the connection between the circle system and the tube, a side arm sampling site is linked to a gas monitoring equipment (e.g., an infra-red monitor or a mass spectrometer). Typically, a sampling speed is 200 mL/min. Desflurane has a membrane factor, M, of 0.2 for most patients. A more precise determination of M is performed at the end of 3 min, when 85–95% of the FRC has been filled with the gas. Measuring the inspired desflurane concentration ($C_i$) and the expired desflurane concentration ($C_e$) of a patient at this time, the patient's membrane factor M can be obtained by the formula $M=(C_i-C_e)/(C_i-C_{b'})$, and $C_{b'}$ is 0. Thus, if the inspired desflurane concentration is 6% and the expired desflurane concentration is recorded as 4.8% at 3–4 minutes, this patient's membrane factor for desflurane is: M-(6-4.8)/6=0.2.

During the course of desflurane anesthesia, the mixed venous desflurane concentration can be assessed according to the formula $C_{b'}=[C_i(M-1)+C_{e'}]/M$.

For example, if the inspired desflurane concentration is 6.2% and the expired desflurane concentration is 5.4%, the desflurane concentration in the mixed venous blood ($C_{b'}$) is: 6.2−5.4=0.2 (6.2−$C_{b'}$), therefore $C_{b'}$=2.2%.

Accordingly, based on formula: $C_b=(C_{e'}+C_{b'})/2$., the desflurane concentration in the brain ($C_b$) is: (2.2+5.4)/2=3.8%.

In another example, isoflurane is used. The inspired isoflurane concentration is 1.5% and the expired isoflurane concentration is as 0.8 at 3–4 minutes. Thus, the patient's membrane factor for isoflurane is: M=(1.5−0.8)/1.5=0.406.

During a point in the course of anesthesia, if the inspired isoflurane concentration is 1.2% and the expired concentration has risen to 0.9%, the isoflurane concentration in the mixed venous blood ($C_{b'}$) is: 1.2−0.9=0.406 (1.2−$C_{b'}$), $C_{b'}$=0.46%, and the brain isoflurane concentration (Cb) is: (0.9+0.46)/2=0.68%.

After 20 minutes, if the inspired isoflurane concentration is 1.1% and the expired isoflurane concentration remains at 0.9%, the isoflurane concentration in the mixed venous blood ($C_{b'}$) is: 1.1−0.9=0.406 (1.1−$C_{b'}$), $C_{b'}$=0.607%, and the brain isoflurane concentration ($C_b$) is: (0.9+0.607)/2=0.75%.

The methods and formulae described above can be implemented using a variety of software and/or hardware configurations.

For example, the techniques described here are not limited to any particular hardware or software configuration; they may find applicability in any computing or processing environment. The techniques may be implemented in hardware, software, or a combination of the two. The techniques may be implemented in programs executing on programmable machines such as mobile or stationary computers, devices such as a detector for the inhalation compound, and similar devices that each include a processor, a storage medium readable by the processor (including volatile and non-volatile memory and/or storage elements), at least one input device, and one or more output devices. Each program may be implemented in a high level procedural or object oriented programming language to communicate with a machine system. However, the programs can be implemented in assembly or machine language, if desired. In any case, the language maybe a compiled or interpreted language. Examples of programming languages include C, C++, Java, Fortran, Pascal, and Visual Basic. The programs can also be implemented within other software applications, e.g., a spreadsheet or database program, e.g., using scripts, formulae, and other software tools.

Each such program may be stored on a storage medium or device that is readable by a general or special purpose programmable machine for configuring and operating the machine when the storage medium or device is read by the computer to perform the procedures described in this document. The system may also be implemented as a machine-readable storage medium, configured with a program, where the storage medium so configured causes a machine to operate in a specific and predefined manner. Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media. The processes described here may be executed by an embedded system.

Without further elaboration, it is believed that one skilled in the art can, based on the description herein, utilize the present invention to its fullest extent. All publications cited herein are hereby incorporated by reference in their entirety.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An article comprising a machine-readable medium that stores machine-executable instructions, the instructions causing a machine to:

receive values representing the concentration of a compound administered in a gas into a subject to fill the pulmonary functional residual capacity, the values including an inspired compound concentration ($C_i$) and an expired compound concentration ($C_e$), wherein the inspired compound concentration ($C_i$) and the expired compound concentration ($C_e$) are obtained after having filled the functional residual capacity with the gas; and output a representation of a compound concentration in the brain ($C_b$), in which the representation of the compound concentration in the brain ($C_b$) is assessed by the formula $C_b=(C_{e'}+C_{b'})/2$, wherein $C_{b'}=[C_i(M-1)+C_{e'}]/M$, M being an alveolar membrane factor for the compound.

2. The article of claim 1, wherein the values further include a second inspired compound concentration ($C_i$) and a second expired compound concentration ($C_e$), in which $C_i$ and $C_e$ are measured at the time when about 90% of the functional residual capacity is filled with the gas, and M is assessed based by the formula M=1−($C_e/C_i$).

3. The article of claim 2, wherein the instructions further cause the machine to:

trigger a detector to sample the compound from an inspiration and an expiration measured at the time when about 90% of the functional residual capacity is filled with the gas;

monitor a time interval; and trigger the detection to sample the compound from an inspiration and an expiration after filling the functional residual capacity with the gas.

4. An apparatus comprising:

a display; and a processor, the processor configured to:

receive values representing the concentration of a compound administered in a gas into a subject to fill the pulmonary functional residual capacity, the values including an inspired compound concentration ($C_i$) and an expired compound concentration ($C_e$), wherein the inspired compound concentration ($C_i$) and the expired compound concentration ($C_e$) are obtained after having filled the functional residual capacity with the gas; and control the display to depict a representation of a compound concentration in the brain ($C_b$), in which the representation of the compound concentration in the brain ($C_b$) is assessed by the formula $C_b=(C_{e'}+C_{b'})/2$, wherein
$C_{b'}=[C_i(M-1)+C_{e'}]/M$, M being an alveolar membrane factor for the compound.

5. The apparatus of claim 4, wherein the values include a second inspired compound concentration ($C_i$) and a second expired compound concentration ($C_e$), in which $C_i$ and $C_e$ are measured at the time when about 90% of the functional residual capacity is filled with the gas, and M is assessed based by the formula $M=1-(C_e/C_i)$.

6. The apparatus of claim 5 further comprising a detector.

7. The apparatus of claim 6, wherein the instructions further cause the machine to:
trigger the detector to sample the compound from an inspiration and an expiration measured at the time when about 90% of the functional residual capacity is filled with the gas;
monitor a time interval; and
trigger the detector to sample the inhalation compound from an inspiration and an expiration after filling the functional residual capacity with the gas.

* * * * *